United States Patent [19]

Rosov

[11] Patent Number: 4,871,662

[45] Date of Patent: Oct. 3, 1989

[54] DEVICE FOR SHIPPING MICROBIOLOGY TEST SAMPLES

[75] Inventor: Eugene Rosov, Manchester, N.H.

[73] Assignee: WaterTest Corporation, Manchester, N.H.

[21] Appl. No.: 96,265

[22] Filed: Sep. 9, 1987

Related U.S. Application Data

[63] Continuation of Ser. No. 895,186, Aug. 11, 1986, abandoned.

[51] Int. Cl.⁴ .............................................. C12Q 1/24
[52] U.S. Cl. ........................................ 435/30; 435/34; 435/294
[58] Field of Search ........... 73/863.23, 863.21, 864.91; 435/31, 34, 803, 805, 809, 810, 30, 35, 292, 294

[56] References Cited

U.S. PATENT DOCUMENTS

| | | | |
|---|---|---|---|
| 2,923,669 | 2/1960 | Poitras | 435/34 |
| 3,783,106 | 1/1974 | Henshilwood | 435/34 |
| 4,036,698 | 7/1977 | Bush et al. | 435/31 |
| 4,215,198 | 7/1980 | Gordon | 435/31 |
| 4,311,792 | 1/1982 | Avery | 435/30 |
| 4,416,995 | 11/1983 | Amaral | 435/35 |
| 4,435,505 | 3/1984 | Zierdt | 435/34 |
| 4,528,268 | 7/1985 | Andersen et al. | 435/31 |
| 4,596,773 | 6/1986 | Wheeler, Jr. | 435/31 |
| 4,604,360 | 8/1986 | Hounsell | 435/294 |

FOREIGN PATENT DOCUMENTS 0614466  11/1979  Switzerland .................. 435/34

Primary Examiner—John Chapman
Assistant Examiner—Robert R. Raevis
Attorney, Agent, or Firm—Nutter, McClennen & Fish

[57] ABSTRACT

The device, which is a multi-element tube, is adapted for receiving a water sample into a first chamber. The sample is then caused to pass through a relatively coarse filter into a second chamber, where the sample contacts a relatively fine second filter on which a portion of the sample is retained. A stabilizing agent is added to the second filter so that the sample is maintained for later testing. The device can then be sent, at ambient temperatures, intact and in a sterile, sealed condition, via common carrier to a central laboratory, where the portion of the second filter is removed for testing. Thus, the present device is a simple to use and inexpensive means for conducting microbiological testing of samples from remote sites. It eliminates the need for laboratory personnel to take and filter and/or take and chill and filter a sample at the site of testing and for mobile laboratory testing facilities, or alternatively, the need for special express shipping arrangements for liquid unfiltered water samples.

20 Claims, 1 Drawing Sheet

DEVICE FOR SHIPPING MICROBIOLOGY TEST SAMPLES

This application is a continuation of application Ser. No. 895,186, filed with the U.S. Patent and Trademark Office on Aug. 11, 1986, now abandoned.

BACKGROUND OF THE INVENTION

1. Field of the Invention

This invention relates to the sampling of water for microbiological quality determinations, and particularly to a method for maintaining the integrity and validity for an extended period of time of a sample of water drawn for the purposes of microbiological testing by a laboratory.

Certain microbiological tests conducted upon water samples have required testing due to the possible loss or change of microbiological contaminants after collection of the samples. For various reasons, such as convenience, it has not always been possible to perform all necessary microbiological testing immediately upon the collection of the water samples. In such circumstances, the Environmental Protection Agency (EPA), which is the responsible governmental regulatory agency, has set forth requirements to stabilize such water samples to ensure accuracy in assessing the contamination from microbiological agents.

Shipping the test samples to the testing site in the past has proved unfeasible, since EPA requires certain samples for certain microbiological contamination determinations be tested within a limited time period. While the EPA has specified procedures for allowing a lengthening of the normal 30-hour "holding" time within which normal microbiological testing must occur to be valid, such procedures have not been readily accessible to the general public and have also been cumbersome and infrequently employed by laboratories, due to the inconvenience of the available and accepted methodologies.

2. Description of the Prior Art

In the past, samples to be later tested required immediate chilling of the sample at the sampling site and maintenance of the sample at 4 degrees centigrade during the immediate transportation to the laboratory. This manner of sample testing has the expense of rapid and special transportation and of the equipment for constant-temperature maintenance of samples while en route to the laboratories. Moreover, the samples do not always arrive in a usable condition, e.g., the means for chilling may be inadequate or the transportation may fail to deliver on time.

The other manner of testing, that is, on-site sampling and testing by laboratory personnel, also involves increased expense. These expenses involve both the time in traveling to and from the site and the maintenance of appropriate mobile apparatus for use by the laboratory personnel.

There has, therefore, been a need to develop a sampling device for collection of water sample for microbiological testing, whereby lay persons may receive sampling devices shipped by common carrier, collect the samples in the devices, and then ship the sample devices to central laboratories by common carrier for testing.

It is thus object of the invention to provide a simple and relatively inexpensive sampling device which permits inexperienced persons to take water samples, while permitting a substantial increase in the time period in which to make valid tests on such samples. It is another object to maintain laboratory samples for transportation to a testing site at a central location remote from the source of the samples.

It is a further object of the invention to provide a physical device which can be mailed or otherwise be shipped to and from a remote sampling site by common carrier and forwarded therefrom with water samples to a central laboratory.

The present invention accordingly comprises the features of construction, combination of elements and arrangement of parts which will be exemplified in the construction hereinafter set forth, and the scope of the invention will be indicated in the claims.

SUMMARY OF THE INVENTION

The present invention solves the above-described problems by providing a physical device which allows even inexperienced persons to take water samples adapted for later testing. The device is provided with a filter through which a sample is drawn. A liquid contained within the device is added to the sample to produce a medium which provides for the microbiological nutritional and bacterio-static conditions of the sample. A valid sample for the determination of microbiological contamination of water can thus be delivered to the laboratory through common carrier delivery at ambient temperatures.

The device, which is a multi-element tube, is adapted for receiving a water sample into a first chamber. The sample is then caused to pass through a relatively coarse, non-wetting filter into a second chamber, where the sample contacts a relatively fine second filter which retains small particles, i.e. of microbial size. A stabilizing agent, contained in a reservoir within the device, is then released to contact the second filter and maintain bacteria retained in the filter for later testing. The device can then be sent, at ambient temperature, intact and in a sterile, sealed condition, via common carrier to a central laboratory for processing of the sample.

Thus, the need for laboratory personnel to take and filter and/or take and chill and filter a sample at the site of testing and for mobile laboratory testing facilities, or, alternatively, the need for special express shipping arrangements for water samples has been eliminated.

BRIEF DESCRIPTION OF THE DRAWINGS

This invention is pointed out with particularity in the appended claims. The above and further advantages of this invention may be better understood by referring to the following description taken in conjunction with the accompanying drawings, in which:

DETAILED DESCRIPTION OF THE PREFERRED EMBODIMENT

Figure 1:
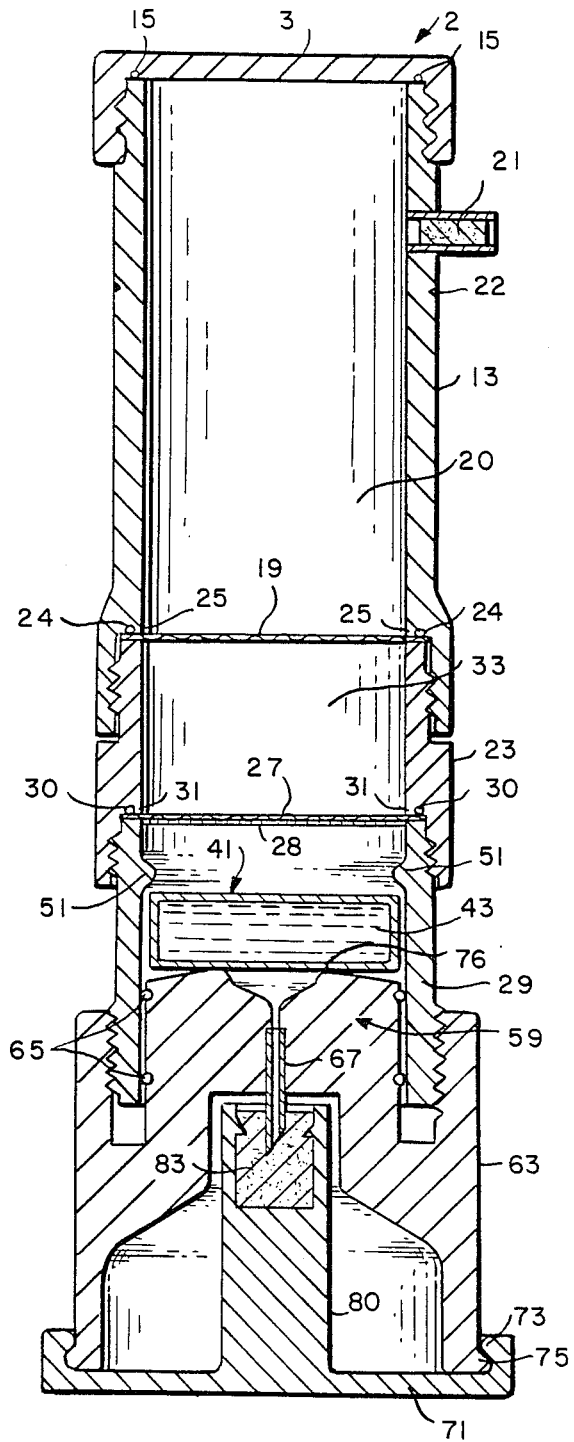
FIG. 1 is a cross-section of a water sample vessel of the present invention.

With reference to FIG. 1, a water sample vessel 2 embodying the present invention is shown with a threaded cap 3 removably secured to a tube 13. An O-ring gasket 15 aids in forming a gas-tight seal between the cap 3 and the tube 13.

The cap 3 and a first filter 19 define a chamber 20 within the tube 13. A porous plug 21 is provided in the wall of tube 13 for venting purposes as described below. A fill indicium line 22 is formed on the tube 13 to indicate an appropriate sample amount to be introduced into the chamber 20.

The filter 19 seats against an O-ring gasket 24 that bears on a shoulder 25 of the tube 13. The filter 19 is held in place by a second tube 23 which is threaded into the tube 13. A second filter 27 together with an absorbent pad 28 are disposed between a third tube 19, which is threaded into the tube 26, and another O-ring gasket 30 which bears on a shoulder 31 of the tube 26. The filters 19 and 27 define a second chamber 33 in the tube 26.

A vial 41, which is filled with a nutrient bacteriostatic holding medium 43, is held in place by a lip 51 extending from the inner wall of tube 19 and by an inner extending portion 59 of a fourth tube 63.

The tube 63 is sealed to the inner wall of the tube 29 by "O"-rings 65. A downwardly extending needle 67, secured in the portion 59 of the tube 63 provides communication with the interior of the tube 29. A cap 71, at the bottom end of the tube 63, has a lip 73 which cooperates with an annular boss 75 of the tube 63 to hold the cap 71 in position. The cap 71 is further provided with an inner extension 80 containing a foam plug 83. When the cap 71 is positioned on the tube 63, the tip of the needle 67 resides in the plug 83. The plug 83 can be treated with a bacteriostatic agent, such as a suitable solution of methyl and propyl parabens, to prevent entry of contaminate into the vessel by way of the needle 67.

In some instances, it may be desirable to have a hose connection in place of a needle 67. This would permit the hose connection to be attached to a suitable vacuum source, either a hand pump or a mechanical pump.

In operation, the user removes the cap 3, and adds a water sample up to the fill-indicium line 22. Applicant has found that a fill indicium marking approximately one-half the volume of the chamber 20 is appropriate. So for the case where the first chamber 20 has a 200 ml capacity, a 100 ml water sample would be added. The filter 19 is a nonself-wetting filter, preferably formed on an inert fluorocarbon material with a nominal pore size 5 to 10 micrometers, so that the water sample, when added, is initially retained in the chamber 20. The cap 3 is then replaced by the user.

The user then removes the bottom cap 71. While maintaining the vessel 2 with the cap 3 upper most, the user applies a vacuum to the needle 67 wsch as by the attachment of an evacuated bottle or other suitable means. The needle 67 in this embodiment is relatively short, a (½ inch) 18 gauge needle which is adapted to be used in penetrating a rubber septum seal of an evacuated vial. During the evacuation the water sample is drawn through the first filter 19 and into the second chamber 33. The first filter acts to prevent larger impurities from passing therethrough while permitting bacteria and the like to pass.

The plug 21, in this case made of polyurethane foam, releases internal pressure when the device is sealed and sterilized by autoclaving prior to sampling and permits air to pass into the first chamber 20, as the water sample is drawn into the second chamber 33. The plug 21 is of sufficiently fine structure to prevent passage of bacteria therethrough.

The water sample, upon entering the chamber 33, contacts the second filter 27 which is, for example, a gridded 0.45 micrometer pore size filter and in this case is formed of cellulose acetate. The support pad 28 which may be secured to the filter 27 is also formed of cellulose acetate. The filter 27 acts to retain bacteria present in the water sample, while the water sample passes through the filter 27. A portion of the water sample is absorbed by the pad. A large portion of the water sample is drawn during the evacuation through the needle 67 and out of the vessel 2. Sufficient air during the evacuation is drawn through the plug 21 to partially dry the pad 28.

After the evacuation is complete, the user replaces the bottom cap 71 and inverts the vessel with the cap 71 upper most. The vial 41 is then ruptured by screwing the tube 63 on the threads of the third tube 29 to force an annular bump 76 on the extension 59 against the bottom surface of the vial. This releases the contents of the vial, i.e., the holding medium 43, which may be, for example, a solution of the following compounds provided in the amounts indicated per liter of distilled water:

| | |
|---|---|
| Tryptose or polypeptone | 10.0 g |
| Thiopeptone or thiotone | 5.0 g |
| Casitone or trypticase | 5.0 g |
| Yeast extract | 1.5 g |
| Lactose | 12.5 g |
| Sodium chloride, NaCl | 5.0 g |
| Dipotassium hydrogen phosphate, $K_2HPO_4$ | 4.375 g |
| Potassium dihydrogen phosphate, $KH_2PO_4$ | 1.375 g |
| Sodium lauryl sulfate | 0.050 g |
| Sodium desoxycholate | 0.100 g |
| Sodium sulfite, $Na_2SO_3$ | 2.10 g |
| Basic fuchsin | 1.05 g |
| Sodium benzoate | 3.84 g | said solution being prepared by rehydrating the above compounds in one liter distilled water containing 20 mL of 95% ethanol. The solution is heated to boiling, promptly removed from heat, and cooled to below 45° C. Sterilization of this solution should not be done by autoclaving and the final pH should be between 7.1 and 7.3. Applicant has found that between 1.8 to 2.4 ml of the media 43 is appropriate. Other EPA approved media may be substituted for the above described solution.

Upon rupture of the vial 41, the medium 43 contacts the filter 27 and bacteria retained therein, as it is absorbed by the pad 28 and mixes with the water sample retained in the pad 28. The vessel 2 can be then placed in a shipping container and returned to the laboratory by ordinary shipping means.

Upon receipt by the laboratory, the cylindrical members 26, 29 and 63 are unscrewed from one another, and the pad 28 is aseptically removed from filter 27. The filter 27 is then placed upon a standard medium for incubation and evaluation.

The remainder of the procedure follows standard and EPA-approved methods for bacterial analysis water.

It has also been found that the first filter is often not necessary in the use of the present invention, as water added to the device frequently is relatively free of larger scale contaminents. In such cases, the device can be constructed without the first filter 19 and the second tube 23 such that the tube 13 is threaded into the tube 29. The user would then remove the cap 3 and add water up to the line 22 in a first chamber having the filter 27 as the lower limit. The filter 27 which is non self-wetting would retain the water sample in the chamber. The structure and the use of the device would otherwise be similar to that described above.

The foregoing description has been limited to a specific embodiment of this invention. It will be apparent, however, that variations and modifications may be made to the invention, with the attainment of some or all of the advantages of the invention. Therefore, it is the object of the appended claims to cover all such variations and modifications as come within the true spirit and scope of the invention.

What is claimed as new and desired to be secured by Letters Patent of the United States is:

1. A device for receiving a water sample, for retaining bacteria from said sample, for stably maintaining said bacteria for a period of time permitting shipment of said bacteria to a laboratory for later bacterial analysis, and for shipping said device with said bacteria therein to said laboratory, said device comprising:
   a first compartment having one end adapted for receiving a water sample;
   a second compartment removably secured at one end to the other end of said first compartment;
   filter means secured between said first and second compartment;
   means for drawing the water sample, positioned in said first compartment, through said filter means and into said second compartment such that bacteria in said sample and a portion of said water sample are absorbed by said filter means;
   means for adding a bacterio-static nutritional medium to said filter means;
   said means for adding includes a sealed vial in which said medium is disposed, means for rupturing said vial, and means for directing said medium to said filter means after said vial has been ruptured, whereby said medium contacts said filter means to maintain said bacteria for later analysis;
   a third compartment movably secured at one end to the other end of said second compartment; and
   means for positioning said vial such that said vial is disposed between said second and third compartments, said means for rupturing includes urging said third and second compartments into closer engagement, and said means for directing said medium include holding said device with said third compartment uppermost so that said medium, after said vial is ruptured, is urged by gravity toward said pad.

2. A device for receiving a water sample, for retaining bacteria from said sample, for stably maintaining said bacteria for a period of time permitting shipment of said bacteria to a laboratory for later analysis, and for shipping said bacteria to said laboratory, said device comprising:
   a first compartment for receiving said sample;
   a second compartment connected to said first compartment;
   a third compartment connected to said second compartment;
   means for drawing said water sample through said compartments;
   filter means separating said first and second compartments and through which said water sample is drawn from said first compartment through said second compartment and into said third compartment by said means for drawing;
   said filter means includes a fine filter which retains bacteria in said sample as said sample is drawn through said filter means;
   a sealed container disposed between said second compartment and said third compartment;
   a nutritional, bacterio-static medium disposed in said container;
   means for remotely and selectively rupturing said container which includes means for urging said second and third compartments together such that members within said compartments bear upon said container; and
   means for adding said medium to said filter means, whereby bacteria retained in said filter means are stably maintained such that said device can be shipped to a testing facility for later analysis.

3. A device according to claim 2 further comprising a fourth compartment positioned between said first compartment and said filter means and a prefilter positioned between said first and fourth compartments wherein said means for drawing draws said sample from said first compartment through said prefilter into said fourth compartment and through said filter means into said second compartment.

4. A device according to claim 2 wherein said filter means also includes an absorbent pad which is removably secured to said filter and said pad absorbs said medium whereby said bacteria retained in said filter are thereby in contact with said medium.

5. A device according to claim 4 wherein said fine filter has a nominal pore size of less than one half micrometer.

6. A device according to claim 4 wherein said means for adding includes said pad which is adapted to absorb said medium whereby said bacteria retained in said fine filter are thereby in contact with said medium.

7. A device for receiving a water sample, for retaining bacteria from said sample, for stably maintaining said bacteria for a period of time permitting shipment of said bacteria to a laboratory for later bacterial analysis, and for shipping said device with said bacteria therein to said laboratory, said device comprising:
   a first cylinder having one end adapted for receiving a water sample;
   a second cylinder removably secured at one end to the other end of said first cylinder;
   filter means secured between said first and second cylinder;
   means for drawing the water sample, positioned in said first cylinder, through said filter means and into said second cylinder such that bacteria in said sample and a portion of said water sample are absorbed by said filter means;
   means for adding a bacterio-static nutritional medium to said filter means;
   said means for adding includes a sealed vial in which said medium is disposed, means for rupturing said vial, and means for directing said medium to said filter means after said vial has been ruptured, whereby said medium contacts said filter means to maintain said bacteria for later analysis;
   a third cylinder movably secured at one end to the other end of said second cylinder; and
   means for positioning said vial such that said vial is disposed between said second and third cylinders and said means for rupturing includes urging said third and second cylinders into closer engagement, and said means for directing said medium include holding said device with said third cylinder uppermost so that said medium, after said vial is ruptured, is urged by gravity toward said pad.

8. A device according to claim 7 further comprising an aperture such that a substantial portion of the water sample passing through said filter by said means for drawing exits said second and third cylinder through said aperture.

9. A device according to claim 8 wherein said aperture is a vacuum fitting.

10. A device according to claim 8, wherein said third and second cylinders are engaged in a threaded manner whereby said second and third cylinders are urged into closer engagement to rupture said vial by screwing the cylinders into closer engagement.

11. A device according to claim 8 wherein said aperture is a vacuum fitting.

12. A device according to claim 7, further comprising a fourth cylinder positioned between said first cylinder and said filter means and secured at one end to said first cylinder and removably secured at the other end to said second cylinder, a cap secured to said third cylinder, and a prefilter secured between said first and fourth cylinders for retaining particulate matter from the water sample passing from said first cylinder to said third cylinder while permitting bacteria to pass therethrough.

13. A device according to claim 7 further comprising a fourth cylinder secured between said second cylinder and said first cylinder such that said filter is positioned between said second and fourth cylinders and a prefilter disposed between said fourth cylinder and said first cylinder, wherein said prefilter permits bacteria to pass therethrough while preventing larger contaminants in said water from passing therethrough wherein said water added to said first cylinder is drawn through said prefilter into said fourth cylinder from said first cylinder and thence through said filter into said second cylinder by said means for drawing.

14. A device according to claim 7 wherein said filter means is removably maintained between said second and first cylinders and includes a fine filter and an absorbent pad removably secured to said fine filter.

15. A device according to claim 14 further comprising a first and second capping means secured on the one end of said first cylinder and the other end of said second cylinder.

16. A method of use of a device by non-technical persons to take and maintain microbiological samples from water samples taken at a remote site for shipment to a central laboratory for analysis, said method comprising the steps of:

(a) removing a first cap from one end of said device;
(b) adding a water sample to a first compartment in the device, while holding the device in a first direction;
(c) removing a second cap from the other end of said device;
(d) replacing the first cap;
(e) drawing the water sample into a second compartment through a filter and an absorbent pad, which is removably secured to said filter;
(f) retaining a microbiological sample in said filter;
(g) draining the water from the second compartment which passed through the filter and pad;
(h) replacing the second cap;
(i) inverting the device;
(j) disposing a vial containing nutritional, bacteriostatic medium in said second compartment;
(k) breaking said vial disposed in said second chamber so that said medium is released therefrom, whereby said medium flows toward said pad and is absorbed thereby;
(l) disposing said filter in contact with said pad whereby said medium and microbiological sample are in contact with one another such that said microbiological sample is stabilized and maintained for shipment to a laboratory; and
(m) shipping said container with said microbiological sample therein to a laboratory for analysis.

17. A container for preparing samples for microbiological analysis, said container being adapted for receiving a water sample, separating a microbiological sample from said water sample, and transporting said retained microbiological sample to a remote laboratory for analysis, said container comprising:

a first cylinder;
a removable cap positioned on one end of said first cylinder adapted for removal to permit addition of the water sample to said first cylinder;
an air-porous plug positioned in the wall of said first cylinder;
a nonself-wetting filter removably positioned in said first cylinder defining a first and second compartment.
an absorbent pad removably secured on said filter for retaining the microbiological sample;
means for drawing water samples added to said first cylinder through said filter;
a second cylinder having one end movably positioned on the other end of said first cylinder;
a third cylinder having one end movably positioned on the other end of said second cylinder;
a vial disposed between said third and second cylinders;
a nutritional, bacterio-static medium disposed in said vial; and
means for securely positioning said vial such that the movement of said second cylinder into closer engagement with said third cylinder ruptures said vial, and said medium is absorbed by said pad, whereby said microbiological sample retained in said filter is maintained for later analysis.

18. A container according to claim 17 further comprising an aperture at the other end of said third cylinder and a cap removably positioned at the other end of said third cylinder wherein said first cylinder includes a fourth cylinder positioned between said filter and the remaining portion of said first cylinder, said second cylinder threadedly engages the one end of said third cylinder, and said means for positioning said vial includes inwardly extending shoulders on said second cylinder and a central protuberance in said third cylinder such that screwing said third and second cylinders into closer engagement ruptures said vial.

19. A container according to claim 17 further comprising an aperture at the other end of said third cylinder; and a second cap removably positioned at the other end of said third cylinder whereby the water sample passing through said second and first cylinders passes into and out of said third cylinder through said aperture when said second cap is removed.

20. A device according to claim 19 wherein said cap positioned on said second cylinder is removed when water is drawn from said first cylinder into and through said second and third cylinders by said means for drawing, said vial is so positioned that water in said second cylinder passes by said vial and into said third cylinder, and said aperture in said third cylinder is positioned so that the water passing said vial and into said third cylinder exits said third cylinder through said aperture.

* * * * *